April 9, 1940. F. H. WITTER Plant Pat. 373
ROSE PLANT
Filed Jan. 10, 1939
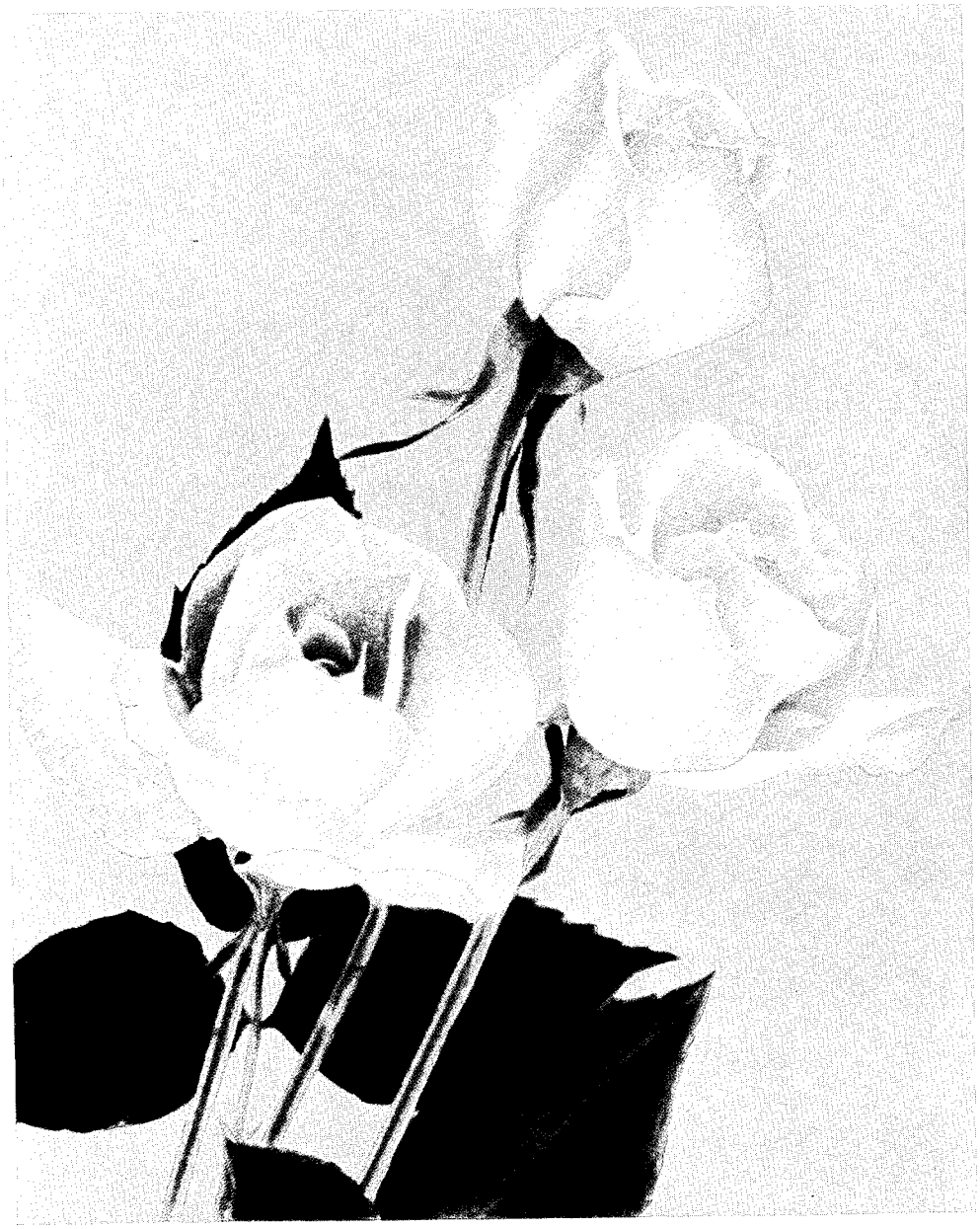
INVENTOR
Frank H Witter
By Orville M Kile
Plant Patent Agent Patented Apr. 9, 1940

Plant Pat. 373

UNITED STATES PATENT OFFICE

373

ROSE PLANT

Frank H. Witter, Evans City, Pa., assignor to Evans City Cut Flower Company, Evans City, Pa.

Application January 10, 1939, Serial No. 250,230

1 Claim. (Cl. 47—61)

My present invention relates to a new and distinct variety of the hybrid tea class of roses. It is a sport of Briarcliff and was discovered by me as a single bud of distinctly darker color. This sport has many of the characteristics of its parent although it differs in several important respects.

The variety has been asexually reproduced for several years and appears to hold its distinguishing characteristics.

The accompanying illustrations show three specimens of this new variety in approximately true colors. It must be understood, however, that the artist has not been able to show the full brilliance and shading of the natural flowers.

Following is a detailed description of the variety. Color plate references are to Ridgway's Color Standards and Nomenclature. Where no plate reference is given, the ordinary dictionary term is intended.

*The plant*

Growth: The growth characteristics of this variety are like those of the parent plant except that the present variety is more vigorous and more prolific. It grows vigorously under all weather conditions and produces an average of 33 blossoms per year.

Foliage: Abundant and attractive.

*Leaves.*—Compound, ordinarily having 3 to 5 leaflets although the first below the peduncle is usually a single leaflet.

*Leaflets.*—Color—very dark green, approximately Empire Green (Plate XXXII) on the upper surface and Light Hellebore Green (Plate XVII) on the under surface, with a slight tinge of purple around the edges on the under side. Shape—oval with acuminate tip. First leaf below peduncle often develops into irregular shapes. Size—terminal leaflets from 2½ to 3¾ inches in length by 1½ to 2¼ inches in width. Usually there are from three to five leaflets and where five appear the two next the stem are very small. The first leaf below the peduncle is usually a single leaflet and many times it is quite small. Edges—regularly and sharply serrated. Texture—thick and leathery.

*Rachis.*—Grooved above and smooth below. Somewhat bronzed.

*Stipules.*—Narrow; clinging, with the exception of their long sharp points. Not so inclined to be foliaceous as in the parent plant.

Sepals: Turn back abruptly in early stages of flower opening. Two or three are inclined to be foliaceous. Leaflike appendages are the color of the leaves, but with a greater amount of purple tinge.

Stems: Very stiff and strong; Biscay Green (Plate XVII). Upper part smooth; thorns on lower part.

*Thorns.*—Pink; sharp; downward pointing.

*The flower*

Bud: Exceptionally long and slender (1¾ inches long just before opening).

*Peduncle.*—Stiff and strong; medium length; smooth.

*Opens.*—Gradually.

*Color.*—Ranges from Rose Color (Plate XII) on the edges, through Spinel Pink (Plate XXVI) to Thulite Pink (Plate XXVI) on the lower part, with a slight yellow base.

Blossom:

*Size.*—Large, fully opened flower being 4½ to 5 inches across and appearing even larger because of the very large outer petals.

*Form.*—Very high centered, retaining its form unusually well throughout the life of the flower. Petals remain outspread without curling.

*Petalage.*—Double, having in November 35 petals, about 15 of which are small and irregularly curled and massed in the center and covered by the longer petals.

*Petals.*—Shape—almost round except that there is a large, sharp point at the center top, giving a spiked effect. Edge is slightly ruffled. The petals of the partly opened flower bulge at the bottom and extend straight upward from the bulge, thus giving the flower in this stage somewhat the shape of a tulip. A little later in the flower's development, the outer petals extend horizontally but the high center is retained. Size—outer petals are unusually large. Measurements are from 2 to 2½ inches in length and about the same in width. Aspect—silky on both surfaces. Substance—petals have delicate appearance but are substantial to the touch.

*Color.*—The blossom of this rose is much darker than that of its parent and includes in its color range many shades not found in the parent blossom. The outside of the petals is Spinel Pink on the edges and Thulite Pink in the central portion (both Plate XXVI), with a very small base of Pale Lemon Yellow (Plate IV). The inside of the outer petals is Rose Color (Plate XII) to Rose Red on the edges, shading through Spinel Pink and Deep Rose Pink and Thulite Pink to a small base of Pale Lemon Yellow. As the opened flower ages it assumes more of the Rose Color and less of the Spinel shades but it never purples.

*Longevity.*—Flower lasts well after being cut.
*Behavior.*—Petals cling and do not curl.
*Fragrance.*—Pleasing, definite and lasting.

*Reproductive organs*

Stamens: Many; surround pistils.
*Filaments.*—Uneven lengths; light yellow, approximately Pinard Yellow (Plate IV).
*Anthers.*—Large; Light Orange-yellow (Plate III).
Pistils: Many; tightly bunched in center of flower.
*Styles.*—Uneven; medium length.
*Stigmas.*—Yellow with reddish tinge along the sides.

*Comparison*

The known varieties which are most like my new rose are Happy Days (Plant Patent No. 144) and Mrs. Frank Schramm (Plant Patent No. 72).

The principal differences between my rose and Happy Days are: (1) the present rose has a much greater spread although it has fewer petals; (2) its petals are larger; (3) its flower center is higher; (4) it grows more vigorously; (5) its foliage is much darker; (6) the color is in a different range.

The principal differences between my rose and Mrs. Frank Schramm are: (1) the present rose is in a different color range and is darker; (2) the sepals are much more foliaceous in the present rose; (3) its foliage is darker green and is larger; (4) its growth is much more vigorous.

Although Briarcliff is less like this variety than the two above mentioned roses, we give comparisons because of the parentage. The principal differences between my new rose and Briarcliff are: (1) my new rose is in a different color range and is considerably darker; (2) its petals are much larger and the blossom has a much greater spread; (3) its growth is more vigorous and its breaks more freely; (4) its blossoms are superior in hot summer weather; (5) it produces more flowers during a year; (6) its foliage is a much darker green.

Having thus disclosed my discovery, I claim:

A new and distinct variety of rose plant as shown and described, characterized particularly by its very vigorous and prolific growth; its exceedingly dark foliage of heavy substance; and its flowers of large size which have a pleasing and lasting fragrance, very large outer petals, a high pointed center retained throughout the life of the flower, and a distinctive color ranging from Thulite Pink to Rose Red.

FRANK H. WITTER.